United States Patent
Beller

(10) Patent No.: US 10,792,320 B2
(45) Date of Patent: Oct. 6, 2020

(54) METHODS FOR TREATMENT OF BLADDER DYSFUNCTION

(71) Applicant: Michael Alan Beller, Jamaica, NY (US)

(72) Inventor: Michael Alan Beller, Jamaica, NY (US)

( * ) Notice: Subject to any disclaimer, the term of this patent is extended or adjusted under 35 U.S.C. 154(b) by 0 days.

(21) Appl. No.: 16/293,195

(22) Filed: Mar. 5, 2019

(65) Prior Publication Data

US 2019/0298788 A1    Oct. 3, 2019

Related U.S. Application Data

(60) Provisional application No. 62/649,113, filed on Mar. 28, 2018.

(51) Int. Cl.
| | |
|---|---|
| *A61K 36/42* | (2006.01) |
| *A61K 31/593* | (2006.01) |
| *A61P 13/10* | (2006.01) |
| *A61K 31/733* | (2006.01) |
| *A61K 31/198* | (2006.01) |

(52) U.S. Cl.
CPC ............ *A61K 36/42* (2013.01); *A61K 31/198* (2013.01); *A61K 31/593* (2013.01); *A61K 31/733* (2013.01); *A61P 13/10* (2018.01)

(58) Field of Classification Search
None
See application file for complete search history.

(56) References Cited

U.S. PATENT DOCUMENTS

| | | | | |
|---|---|---|---|---|
| 2010/0297140 | A1* | 11/2010 | Scammell | A61K 35/20 424/157.1 |
| 2014/0349375 | A1* | 11/2014 | Benjamin | C12P 7/06 435/244 |
| 2018/0263944 | A1* | 9/2018 | Tripp | A61K 31/51 |
| 2019/0183952 | A1* | 6/2019 | Jiang | A61K 36/185 |

OTHER PUBLICATIONS

U.S. Appl. No. 09/259,857, Mar. 1, 1999, Lam; Thanh Kevin.
Clay McNight, Benefits of L-Arginine and L-Citrulline, Livestrong Foundation, Jun. 22, 2015.
Maranon JA, Lozano C, Martinez-Campesino L., Delos Santos L., Bank G & Caballero-Garrido E., Clinical Study: Effect of supplementation with High Genistein Soybean Isoflavones and Pumpkin Standardized Extract on Urinary Incontinence in Western Perimenopausal Women, Journal of Gynecology and Women's Health, Apr. 12, 2017, Research article vol. 4 Issue 1 Mar. 2017, DOL:10.19080/IGWIL2017.04.555627.
Martin Leibbrand, Simone Siefer, Christiane Schon, Tania Perrinjaquet-Moccetti, Albert Kompek, Anca Csernich, Franz Bucar & Matthias Heinrich Kreuter, Effect of an Oil Free Hydroethanolic Pumpkin Seed Extract on Symptom Frequency and Severity in Men with Benign Prostatic Hyperplasia: A Pilot Study in Humans, Journal of Medicinal Food, J Med food 22 (6) 2019, 551-559, Mary Ann Liebert, Inc., and Korean Society of Food Science and Nutrition DOI: 10.1089/jmf.2018.0106.
Shabir Daya, Treating an Overactive Bladder (https://www.victoriahealth.com/editorial/treating-overactive-bladder).
Mark Stengler, NMD, Pumpkin Seed Oil for Urinary Incontinence (http://markstengler.com/featured/pumpkin-seed-oil-for-urinary-incontinence).
Jeremy Fields, MD, Jorge T. GO, MD, MSc, & Konrad S. Schulze, MD, Pill Properties that Cause Dysphagia and Treatment Failure, Curr Ther Res Clin Exp. Dec. 2015; 77: 79-82, published online Aug. 20, 2015 Doi: 10.1016/j.curtheres.2015.08.002.
Jennifer Le, PharmD, MAS, BCPS-ID, FIDSA, FCCP, FCSHP, Skaggs School of Pharmacy and Pharmaceutical Sciences, University of California San Diego, Drug Absorption, Merck Manual Consumer Version, Last full review Jan. 2018. (https://www.merckmanuals.com/home/drugs/administration-and-kinetics-of-drugs/drug-absorption).
Medicare Europe, Liquid vs Pills, (http://medicare-europe.co.uk/science-clinical-data/liquid-vs-pills.html).
Rathish Nair and Arun Maseeh, Vitamin D: The "sunshine" vitamin, J Pharmacol Pharmacother. Apr.-Jun. 2012; 3(2): 118-126 doi: 10.4103/0976-500X.95506.
Dr. Susie Gronski, DPT, PRPC, WCS, Vitamin D Can Help Decrease Risk of Pelvic Floor Disorders in Women, Women's Health Blog.
G. Alessandro Digesu, Elena Verdi, Linda Cardozo, Lorenza Olivieri, Vik Khullar, Enrico Colli, Phase IIb, Multicenter, Double-blind, Randomized Placebo-controlled, Parallel-group Study to Determine Effects of Elocalcitol in Women With Overactive Bladder and Idiopathic Detrusor Overactivity, Jul. 2012, vol. 80, Issue 1, pp. 48-54 (http://www.goldjournal.net/article/S0090-4295(12)00374-3/abstract).
Sudhass Sharma, Neelam Aggarwa, Department of Obstetrics and Gynaecology, Vitamin D and Pelvic Floor Disorders, (http://www.researchgate.net/publication/319861434_Vitamin_D_and_Pelvic_Floor_Disorders).
Swati Sharma, Neerja Goel, SV Madhu, Shalini Rajaram, Satendra Sharma, Serum elastin and 25 hydroxyvitamin D levels in women with pelvic organ prolapse, JIACM 2013; 14(3-4) 224-8.
Web MD Pumpkin (http://www.webmd.com/vitamins/ai/ingredientmono-810/pumpkin).
William Faloon, A Breakthrough in the Relief of Overactive Bladder and Urinary Incontinence, Life Extension Magazine Nov. 2008 (http://www.lifeextension.com).
Vahlensieck, W., Theurer, C., Pfitzer, E., Banik, N., Engelmann U., Effects of pumpkin seed in men with lower urinary tract symptoms due to benign prostatic hyperplasia in the one-year, randomized placebo-controlled GRANU study. Urol Int. 2015; 94(3):286-295. Doi: 10.1159/000362903. Epub Sep. 5, 2014 (https://www.ncbi.nlm.nih.gov/pubmed/25196580).
.Rosemont Pharmaceuticals Limited, I Can't Swallow Tablets: Difficulty Swallow Tablets, (https://www.rosemontpharma.com/patients/swallowing-difficulties).

(Continued)

*Primary Examiner* — Ralph J Gitomer

(57) ABSTRACT

A nutritional supplement and method of treating or preventing urogenital system disorders including urinary incontinence, overactive bladder, enuresis, benign prostatic hyperplasia, nocturia, cystitis, and urinary calculi, without unwanted side effects. The supplement comprises vitamin D3, nitric oxide precursor, pumpkin seed extract and prebiotic fiber in a particular composition.

12 Claims, No Drawings

(56) References Cited

OTHER PUBLICATIONS

Candace Y. Parker-Autry, MD, Kathryn L. Burgio PhD, Holly E. Richter, PhD, MD, Vitamin D Status—A Clinical Review with Implications for the Pelvic Floor, Int Urogynecol J. Nov. 2012: 23(11): 1517-1526, published online Mar. 14, 2012. doi: 10.1007/s00192-012-1710-6.

Jennifer Warner, WEB MD, Low Vitamin D Levels Tied to Incontinence (http://www.webmd.com/urinary-incontinence-oab-news/20100322/low-vitamin-d-linked-incontinence).

Samuel S. Badalian, MD, PhD & Paula F. Rosenbaum, PhD, Vitamin D and Pelvic Floor Disorders in Women (Results from the National Health and Nutrition Examination Survey) (Obstetrics & Gynecology: Apr. 2010—vol. 115—Issue 4—p. 795 doi: 10.1097/AOG.obo13e3181d34806.

Preethi Raja Navaneethan, Aruna Kekre, Kuruthukulangara Sebastian Jacob, and Lilly Varghese, Vitamin D deficiency in postmenopausal women with pelvic floor disorders, J Midlife Health. Apr.-Jun. 2015; 6(2): 66-69 doi: 10.4103/0976-7800.158948 (https://www.ncbi.nlm.nih.gov/pmc/articles/PMC4481742/).

\* cited by examiner

METHODS FOR TREATMENT OF BLADDER DYSFUNCTION

FIELD OF THE INVENTION

The present disclosure relates to nutritional supplements and more particularly to a nutritional supplement composition for bladder control, and a method of treating bladder dysfunction.

BACKGROUND OF THE INVENTION

Studies reveal that cellular deficiencies affect a network of functions in the human body. Bladder dysfunction is caused by abnormal functioning of the bladder tissue resulting in dysuria, irritative symptoms of urgency, frequency and nocturia and the obstructive symptoms of reduced flow rate, incomplete emptying, hesitancy and increase time to urinate. One type of bladder dysfunction is overactive bladder (OAB).

Overactive bladder may be due to a number of factors. One such cause of overactive bladder is benign prostate hyperplasia (BPH), a common condition in aging men. The bladder dysfunction symptoms are related to the effect of the enlarged prostate on the urethra which creates a partial urethral obstruction. Other causes of outlet obstruction that results in bladder dysfunction include but are not limited to cancer, sclerosis or fibrosis of the bladder neck, urethral structure disease, urethral valves, and smooth and striated sphincter dyssynergia. An overactive bladder might also occur as a result of neurological damage due to disorders including but not limited to stroke, Parkinson's disease, diabetes, multiple sclerosis, peripheral neuropathy, or spinal cord lesions.

When the bladder is functioning normally, the muscles in the bladder wall remain relaxed, allowing the bladder to expand and store urine. During urination, the muscles contract, the bladder sphincters open, and urine is voluntarily released. People who have overactive bladder syndrome (OAB) experience "urgency" which is the sudden, strong urge to urinate. If the urge cannot be suppressed due the over activity and weakening of the detrusor muscle, involuntary leakage of urine results. Other symptoms of OAB include the need to urinate many times during the day (urinary frequency) and at night (nocturia). There are many nutritional supplements on the market that purport to promote general health. These supplements typically take the form of tablets, capsules, or powders that are combined with meals as part of a healthy diet regimen.

Apart from nutritional supplements that are designed to promote general health, there are also dietary products on the market directed at bladder control. One of the leading products generally uses a tincture in a liquid form that contains an alcohol base. Other products in the form of pills or tablets do not have the effect of absorbing as much into the patient body compared with a pure liquid. While these products may suppress incontinence, the lack of variance in ingredients fails to create a continuous homeostasis process that creates uniformity while the body is in constant flux. These products may be effective for a short time by absorbing liquid content in the bladder, creating a less frequent urge to urinate, but ultimately users experience return of their urogenital disorder symptoms.

Accordingly, there remains a need for a natural composition specifically formulated for treating bladder dysfunction without the use of pharmaceutical drugs, which require a prescription and accord high incidences of side effects without effectively addressing the underlying bladder disorder or attacking the issue through different mechanisms of action to achieve the desired results.

SUMMARY OF THE INVENTION

A nutritional supplement composition combining amino acids, vitamins, plant extracts, and essential nutrients along with gentle digestive enzymes is disclosed. This over the counter dietary supplement is made up various types of natural ingredients and when combined, supports healthy bladder control and overall health. The supplement provides a completely natural bladder control aid that suppresses urgency, frequency, and leakage. Other essential nutrients may be further included.

The combination of the aforementioned specific components yields a composition directed particularly at bladder control, relaxation, support and strengthening. This composition contains components that were not previously known or expected to additively or synergistically increase or enhance the composition's effectiveness.

In one aspect thereof, a nutritional supplement for inhibiting incontinence includes a combination of vitamin D3, prebiotic fiber, pumpkin seed extract, and nitric oxide precursor. In a particular aspect thereof, a nutritional supplement for inhibiting incontinence includes a combination of vitamin D3, prebiotic inulin, pumpkin seed extract, and L-citrulline.

In one embodiment, the supplement includes in a single serving size of 30 ml including active ingredients comprised of about 550 mg of pumpkin seed extract, 500 mg L-citrulline, 1500 mg prebiotic inulin and 1500 IU of vitamin D3. This additive and synergistic combination of ingredients is found to be surprisingly effective at mitigating or alleviating the effects of frequency, urgency and incomplete releasing of urine from the bladder. In addition, this formulation strengthens the pelvic floor and sphincters by inhibiting key enzymes (aromatase) which helps conserve testosterone and builds muscles.

Additional features and benefits of the presently disclosed nutritional supplement will become apparent from the detailed description, and claims set forth below.

DETAILED DESCRIPTION OF THE INVENTION

Embodiments in accordance with the presently disclosed nutritional supplement include nutritional supplements that are particularly useful in preventing or treating urinary incontinence. In the following description, numerous specific details are set forth such as specific formulations, processing steps, process parameters, etc., in order to provide a thorough understanding of the presently disclosed nutritional supplement. One skilled in the art will understand that these specific details need not be employed to practice the presently disclosed nutritional supplement.

Unless otherwise defined, all technical and scientific terms used herein have the same meaning as commonly understood by one of ordinary skill in the art to which this invention belongs. The terminology used in the description herein is for describing particular embodiments only and is not intended to be limiting. As used in the description and the appended claims, the singular forms "a," "an," and "the" are intended to include the plural forms as well, unless the context clearly indicates otherwise.

Except where otherwise indicated, all numbers expressing quantities of ingredients and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions. Any numerical value, however, inherently contains certain errors necessarily resulting from the standard deviation found in their respective testing measurements. Notwithstanding that the numerical ranges and parameters setting forth the broad scope are approximations, the numerical values set forth in the specific examples are reported as precisely as possible.

Every numerical range given throughout this specification will include every narrower numerical range that falls within such broader numerical range, as if such narrower numerical ranges were all expressly written herein. Additionally, the recitation of numerical ranges within this specification is considered to be a disclosure of all numerical values and ranges within that range. For example, if a range is from about 50 mg to about 10,000 mg, it is deemed to include, for example; 51 mg, 75 mg, 130 mg, 1,400 mg, or any other value or range within the range.

The composition of the presently disclosed nutritional supplement supplies an additive and synergistic composition of compounds that together create a natural, healthy and holistic approach to traditional drug therapy.

The network deficiencies of amino acids, plant extracts, vitamins, and other essential nutrients recognized by this inventor are so common that a majority of people in the general population have clinically been documented to be deficient. It therefore is not surprising that a significant portion of the U.S. population suffers from incontinence, and that their efforts to control their leakage by using prescription medications rather than through conventional natural ingredients are often unsuccessful. Targeting several deficiencies is the key rather than concentrating on one single mechanism of action. However, since the general population is not a person of the art, they do not know how to make the proper natural composition to receive the maximum beneficial effects.

Example 1 presents one embodiment of the composition range of the presently disclosed nutritional supplement.

A basic example of the present disclosure having demonstrated a synergistic effect with regard to overactive bladder is as follows:

Example I

|  | weight |
|---|---|
| Pumpkin Seed Extract | 550 mg |
| L-citrulline (nitric oxide precursor) | 500 mg |
| Vitamin D3 | 1,500 IU |
| Prebiotic inulin (prebiotic fiber) | 1,500 mg |

The amounts of vitamin D3, pumpkin seed extract, L-citrulline, and prebiotic inulin may be varied within any suitable range to provide the desired effect.

The composition may be in any convenient nutritional supplement form.

The administration routes of the composition alternatively include enteral, e.g. oral or rectal, parental, or transdermal patch or extended/sustained release.

Examples of vehicles for oral route include tablets, soft gels, patches, liquid formulation, and capsules, wherein, for example, a serving size is two capsules. To make capsules, the above components may be mixed with food stuffs or an inert carrier (e.g., starch or calcium carbonate or lactose) in a conventional manner as known in the art.

In making capsules, tablets, soft gels, patches and liquid formulation, it is well known in the art that other inactive ingredients are necessary to make it palatable and to provide stability. Suitable binders, lubricant and other inactive components would be incorporated into the formulation. In addition, flavoring, preservatives, flow enhancers, filling aids and other agents may be also be desired.

It is to be appreciated that other suitable forms, such as powder or liquid, prepared in conventional manners, with or without food stuffs or inert carriers, are also contemplated.

Alternatively, a composition of the present disclosure can be rendered in a liquid form, suitable for patients that are unable to swallow a solid pill.

The contribution of each of the individual components is described as follows.

Pumpkin seed extract that is water-soluble exerts anabolic (tissue-building) effect on the pelvic floor muscles via several mechanisms. First, by inhibiting the aromatase enzyme, it may make more testosterone available to strengthen the pelvic muscles. Secondly, this water-soluble pumpkin seed fraction binds to the androgen receptor on pelvic muscle cells, thus inducing a strengthening effect. A preferred pumpkin seed product is EFLA®940—HYPERPURE manufactured by Frutarom. The pumpkin seed extract may be present preferably in a dose range of 100 mg-1,000 mg per day.

The nitric oxide precursor may preferably be present in an amount of about 50 mg-10,000 mg. Particularly preferred nitric oxide precursor L-citrulline in the body acts as an arginine precursor, meaning it is used in the production of arginine because it is the end product from L-citrulline being broken down in the kidneys. Its critical role in the human body is that of a nitric oxide precursor. Arginine may be used instead with similar results, as might other known nitric oxide precursors. The nitric oxide may comprise one or more known nitric oxide precursors.

Prebiotic fiber is a soluble carbohydrate fiber, one of three types of dietary fiber, including soluble, insoluble, and resistant starch. For a carbohydrate to have soluble fiber properties it must dissolve in water to form a gelatinous material. In the present disclosure, inulin is a preferred prebiotic fiber. Other prebiotic fibers include fructooligosaccharides, polydextrose, arabinogalactan, lactitol, transgalactooligosaccharides (TOS), isomaltooligosacchharides (IMO), xylooligosaccharides (XOS), alpha-glucooligosaccharides, soy bean oligosaccharides, arabinoxylan-oligosaccharide. The prebiotic fiber may comprise one or more prebiotic fibers.

Prebiotic inulin is a member of the prebiotic family and promotes a healthy digestive system, reduces high blood pressure, and increases energy through proper utilization of food. Prebiotic inulin has not previously been associated with the treatment of bladder disorder. While its effect in promoting an additive or synergistic effect to the remainder of the components of the composition is not fully understood, it is hypothesized that prebiotic inulin promotes a synergistic effect to the remainder of the presently described composition as follows. Inulin functions in the gastrointestinal tract include by modulating microbial fermentation, reducing fat and cholesterol absorption, and reducing pH; these effects may therefore have an effect on reducing intestinal disturbances, hyperlipidemia, hyperglycemia and intestinal cancer.

The solubility of prebiotic inulin is considered to be even higher than many other types of prebiotic fibers, meaning it absorbs water more easily than other carbohydrates and in conjunction with pepsin already in the human stomach helps form stool that can easily be passed through a digestive tract. Due to its chemical composition, when prebiotic inulin is mixed with liquid it forms a creamy gel. It is hypothesized by the present inventor that this form results in reduced pressure and tension being placed on the bladder, which is one direct connection with bladder leakage. In effect, the inclusion of prebiotic inulin dramatically increases the effectiveness of its co-components. Prebiotic inulin is preferably contained in a dose amount of about 500 mg to 15,000 mg per day.

Vitamins are vital elements to obtain a proper muscle function. The vitamin D family in particular helps the muscle and skeletal system in many ways. For example, vitamin D can regenerate muscles tissue, which increase functioning all over the body. Vitamin D plays a role in cosmetic care by promoting healthy skin, which is one of the areas that are body can absorb it from. Of particular use in the present composition is vitamin D3.

There are vitamin D receptors in the detrusor wall of the bladder and urethra. These receptors require Vitamin D3 for muscle strengthening and improved bladder and urethra support. Muscle control and strength are vital for the voluntary control of the urethral sphincter and pelvic floor muscles and likely a significant factor in achieving continence. Vitamin D3 is preferably present in an amount of about 300 IU-10,000 IU daily The composition according to one embodiment of the presently disclosed nutritional supplement exhibits distinct additive and synergism among its components for maximum results in bladder control and strengthening. The multiplicative effect of the components of the present disclosure produces results that were heretofore unachievable with the bladder control supplements in the prior art. This is because the prior art supplements used only one component to address one area (e.g., pelvic strengthening) and did not consider how to maximize results or how treatment of the one area would affect other areas (e.g., well-being of intestinal health). The composition of the present disclosure, on the other hand, views bladder control, muscle relaxing, improved colonic motility, pelvic strengthening and overall health/well-being as a complete package and recognizes that changes in one area affect other areas.

Thus, the above composition describes an embodiment of the composition of the presently disclosed nutritional supplement that increases the muscle strength and other enzymes and other agents necessary to metabolize and utilize the inherent biological formalities of the body to solve multiple problems of the bladder. Combining the above components with essential vitamins, amino acids and in establishing a proper regulation of the digestive system, the composition of the presently disclosed nutritional supplement enhances the muscle strengthening of the bladder process in continuous and regulated manner.

It should be understood that detailed description herein is to be regarded in an illustrative rather than a restrictive manner and is not intended to be limiting to the particular forms and examples disclosed. On the contrary, further modifications, changes, rearrangements, substitutions, alternatives and embodiments may be apparent to those of ordinary skill in the art, without departing from the spirit and scope hereof, as defined by the following claims. Thus, it is intended that the following claims be interpreted to embrace all such further modifications, changes, rearrangements, substitutions, alternatives and embodiments.

I claim:

1. A method of treating overactive bladder comprising administering to a patient suffering from overactive bladder a composition comprising a synergistic combination of therapeutically effective amounts of pumpkin seed extract, nitric oxide precursor, vitamin D3, and prebiotic fiber at sufficient intervals to reduce the patient's symptoms of overactive bladder.

2. The method of claim 1, wherein the nitric oxide precursor is L-citrulline.

3. The method of claim 1, wherein the therapeutically effective amounts are:

| | |
|---|---|
| pumpkin seed extract | 100 mg-1,000 mg, |
| L-citrulline | 50 mg-10,000 mg, |
| vitamin D3 | 300 IU-10,000 IU, and |
| prebiotic inulin | 500 mg-15,000 mg. |

4. The method of claim 2, wherein the composition further comprises L-arginine.

5. The method of claim 3, wherein the composition further comprises L-arginine.

6. The method of claim 5, wherein the composition is orally administered to the patient.

7. A method of treating overactive bladder comprising administering to a patient suffering from overactive bladder a composition comprising a synergistic combination of therapeutically effective amounts of pumpkin seed extract, nitric oxide precursor, vitamin D3, and prebiotic inulin at sufficient intervals to treat the patient's overactive bladder.

8. The method of claim 7, wherein the nitric oxide precursor is L-citrulline.

9. The method of claim 8, wherein the therapeutically effective amounts are:

| | |
|---|---|
| pumpkin seed extract | 100 mg-1,000 mg, |
| L-citrulline | 50 mg-10,000 mg, |
| vitamin D3 | 300 IU-10,000 IU, and |
| prebiotic inulin | 500 mg-15,000 mg. |

10. The method of claim 8, wherein the composition further comprises L-arginine.

11. The method of claim 9, wherein the composition further comprises L-arginine.

12. The method of claim 11, wherein the composition is orally administered to the patient.

* * * * *